United States Patent [19]

Saito et al.

[11] Patent Number: 4,511,671
[45] Date of Patent: Apr. 16, 1985

[54] CATALYST FOR MANUFACTURING METHACROLEIN

[75] Inventors: Noboru Saito, Takatsuki; Takeshi Satake, Kyoto; Ryuji Aoki, Himeji; Isao Nagai, Suita, all of Japan

[73] Assignee: Nippon Shokubai Kagaku Kogyo Co., Ltd., Osaka, Japan

[21] Appl. No.: 528,560

[22] Filed: Sep. 1, 1983

[30] Foreign Application Priority Data

Sep. 6, 1982 [JP] Japan .................. 57-153819

[51] Int. Cl.³ .................. B01J 21/08; B01J 23/78; B01J 23/84; B01J 23/88
[52] U.S. Cl. .................. 502/242; 502/215; 502/241; 502/243; 502/246; 502/304; 502/306; 502/307; 502/308; 502/309; 502/310; 502/311; 502/527; 568/479
[58] Field of Search .............. 502/211, 215, 241, 242, 502/243, 246, 304, 311, 527, 306, 307, 308, 309, 310; 568/479

[56] References Cited

U.S. PATENT DOCUMENTS

| | | | |
|---|---|---|---|
| 3,907,712 | 9/1975 | Ohara et al. | 502/243 |
| 3,980,709 | 9/1976 | Kubo et al. | 502/311 X |
| 4,001,317 | 1/1977 | Grasselli et al. | 502/304 X |
| 4,012,449 | 3/1977 | Shikakura et al. | 502/205 X |
| 4,035,418 | 7/1977 | Okada et al. | 502/306 X |
| 4,111,984 | 9/1978 | Ishii et al. | 502/310 X |
| 4,217,309 | 8/1980 | Umemura et al. | 502/309 X |
| 4,414,134 | 11/1983 | Friedrich et al. | 502/215 X |

FOREIGN PATENT DOCUMENTS 2030885  4/1980  United Kingdom .............. 502/311

Primary Examiner—W. J. Shine
Attorney, Agent, or Firm—Sherman & Shalloway

[57] ABSTRACT

A catalyst for manufacturing methacrolein by the vapor phase oxidation of isobutylene or tertiary butanol, said catalyst having the composition represented by the following formula $$Mo_aW_bBi_cFe_dA_eB_fC_gD_hO_x$$

wherein
A represents at least one element selected from the group consisting of nickel and cobalt,
B represents at least one element selected from the group consisting of alkali metals, alkaline earth metals and thallium,
C represents at least one element selected from the group consisting of tellurium, antimony, tin, cerium, lead, manganese and zinc,
D represents at least one element selected from the group consisting of silicon, aluminum, zirconium and titanium,
a, b, c, d, e, f, g, h, and x respectively represent the atomic ratios of Mo, W, Bi, Fe, A, B, C, D, and O, and when
a is fixed at 12,
b is from 0 to 10,
c is from 0.1 to 10,
d is from 0.1 to 20,
e is from 2 to 20,
f is from 0 to 10,
g is greater than 0 to 4,
h is from 0 to 30 and
x is a number determined by the atomic valences of the individual elements, and being molded in the shape of a hollow cylinder having an outside diameter of 3.0 to 10.0 mm, an inside diameter 0.1 to 0.7 times the outside diameter and a length 0.5 to 2.0 times the outside diameter.

6 Claims, 1 Drawing Figure

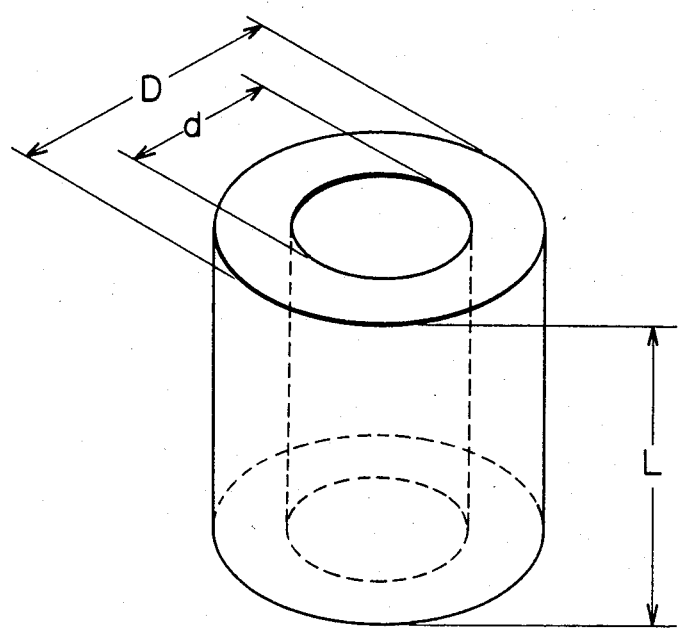

CATALYST FOR MANUFACTURING METHACROLEIN

FIELD OF THE INVENTION

This invention relates to a catalyst for use in obtaining methacrolein at a high selectivity and yield by the catalytic vapor-phase oxidation of isobutylene or tertiary butanol with air or a gas containing molecular oxygen.

DISCUSSION OF PRIOR ART

Many catalysts have already been proposed for the production of methacrolein by the catalytic vapor-phase oxidation of isobutylene or tertiary butanol, and some of them have come into industrial acceptance. Such catalysts are disclosed, for example, in the specifications of U.S. Pat. Nos. 3,907,712, 4,001,317, 4,012,449, 4,035,418 and 4,217,309.

Although these catalysts are actually used in industrial operations, they are unable to give methacrolein at high selectivities and yields, as described in the specific working examples in these patent documents. In actual industrial practice, the catalytic vapor-phase oxidation reaction is very exothermic to cause the formation of unusually heated high-temperature localities, called hot spots, in the catalyst layer, and the oxidation reaction proceeds excessively. Or since the height of the catalyst layer is large and the pressure in the catalyst layer varies from the inlet of the layer toward its outlet, the reaction becomes remote from an ideal one.

SUMMARY OF INVENTION

It is an object of this invention therefore to eliminate such disadvantages, and to provide a catalyst for producing methacrolein at a high selectivity and a high yield.

The present inventors have found that the above object is achieved by a molded article having a specified shape different from the spherical or solid cylindrical shape in the prior art, which is obtained from a catalyst composition having specified constituent proportions.

BRIEF DESCRIPTION OF THE DRAWING

The accompanying drawing is a perspective view for illustrating the catalyst of this invention.

DETAILED DESCRIPTION OF THE INVENTION

According to this invention, there is provided a catalyst for manufacturing methacrolein by the vapor phase oxidation of isobutylene or tertiary butanol, said catalyst having the composition represented by the following general formula

$Mo_aW_bBi_cFe_dA_eB_fC_gD_hO_x$ wherein

A represents at least one element selected from the group consisting of nickel and cobalt, B represents at least one element selected from the group consisting of alkali metals, alkaline earth metals and thallium, C represents at least one element selected from the group consisting of phosphorus, tellurium, antimony, tin, cerium, lead, niobium, manganese and zinc, D represents at least one element selected from the group consisting of silicon, aluminum, zirconium and titanium, a, b, c, d, e, f, g, h, and x respectively represent the atomic ratios of Mo, W, Bi, Fe, A, B, C, D, and O, and when a is fixed at 12,
b is from 0 to 10,
c is from 0.1 to 10,
d is from 0.1 to 20,
e is from 2 to 20,
f is from 0 to 10,
g is from 0 to 4,
h is from 0 to 30, and
x is a number determined by the atomic valences of the individual elements, and being molded in the shape of a hollow cylinder having an outside diameter D of from 3.0 to 10.0 mm, an inside diameter d 0.1 to 0.7 times the outside diameter and a length L 0.5 to 2.0 times the outside diameter.

If L is smaller than D, L is properly termed "thickness" rather than "length", and the shape of the molded catalyst is properly termed the shape of a "ring" rather than the "hollow cylinder".

The catalyst of this invention has the advantage that since its shape is a hollow cylinder or a ring, its geometrical surface area increases, and with it, the conversion of isobutylene or tertiary butanol increases, and that methacrolein formed in the pores of the catalyst diffuses therein more rapidly than in the case of a solid cylindrical catalyst, and the consecutive reaction from methacrolein to methacrylic acid, acetic acid, carbon dioxide and carbon monoxide is reduced.

According to the catalyst of this invention, the pressure drop in the catalyst layer decreases and the cost of the electric power consumption of blowers in industrial production can be reduced, although this can naturally be expected from the hollow cylindrical or ring-like shape of the catalyst of this invention. Example 9 and Comparative Example 1 given hereinbelow show that the pressure drop in a layer of a cylindrical catalyst having a diameter of 6.0 mm and a length of 6.6 mm is on the same level as that in a layer of a hollow cylindrical catalyst having an outside diameter (D) of 5.0 mm, an inside diameter (d) of 2.0 mm and a length (L) of 5.5 mm. Thus, according to this invention, it is possible to reduce the size of the catalyst particles to a greater extent and thus increase the geometrical surface area of the catalyst, and therefore to correspondingly obtain higher activity and higher yields.

The catalyst of this invention further has the advantage of possessing a long active lifetime. Since it is of a hollow cylindrical or a ring-like shape, the effect of removing heat from the unusually high-temperature localities, or the hot spots, is increased and the heat generation by a consecutive reaction to methacrylic acid, acetic acid, carbon dioxide and carbon monoxide is reduced. Consequently, the temperature of the hot spots decreases, the rate of increase of the pressure drop caused by the sublimation of molybdenum, one catalyst ingredient, during the reaction is reduced, and the life of the catalyst is prolonged.

The catalyst of this invention is prepared by known methods. For example, a catalyst composition in the form of a powder or clay obtained by precipitation, kneading, etc., after, if desired, adding small amounts of carbon black, stearic acid, starch, polyacrylic acid, a mineral or vegetable oil, water, etc., is molded into a hollow cylindrical or a ring-like shape by a tableting machine, an extrusion molding machine, etc. and calcined in a stream of air or nitrogen at a temperature of 400° to 700° C. to give a catalyst as a catalyst oxide of the composition $Mo_aW_bBi_cFe_dA_eB_fC_gD_hO_x$.

Starting materials for the catalyst of this invention are desirably compounds which can be converted to oxides in the catalyst preparation process as described above. Examples include the nitrates, ammonium salts, organic acid salts, hydroxides, oxides, metallic acids, and ammonium salts of the metal acids. Illustrative of the alkali metal are lithium, sodium, potassium, rubidium and cesium. Potassium, rubidium and cesium are preferred. Examples of the alkaline earth metal are magnesium, calcium, barium and strontium. Calcium and barium are preferred.

In the present invention, the shape of the catalyst is of utmost importance. Comparative Examples show that if the catalyst has the composition specified above but is not in the hollow cylindrical or ring-like shape specified above, it cannot exhibit the performance desired in this invention. The catalyst of this invention exhibits a very good catalytic performance when it is molded into such a hollow cylindrical shape that the average thickness, i.e.

$$\frac{D-d}{2},$$

is from 1.0 to 4.0 mm. Preferably, the wall thickness is at least 1.0 mm because too small a wall thickness will result in a reduction in the strength of the catalyst.

Isobutylene or tertiary butanol is oxidized in the vapor phase in the presence of the catalyst of this invention by passing a gaseous mixture composed of 1 to 10% by volume of isobutylene or tertiary butanol, 3 to 20% by volume of molecular oxygen, 0 to 60% by volume of steam and 20 to 80% by volume of an inert gas (such as nitrogen or carbon dioxide) over the catalyst at a temperature of 250° to 450° C. and a pressure of atmospheric pressure to 10 atmospheres with a space velocity of 300 to 5,000 $hr^{-1}$.

The following Examples and Comparative Examples illustrate the present invention more specifically. It should be understood however that the invention is by no means limited to these specific examples.

The conversion, selectivity and one-pass yield, as used in this invention, are defined as follows:

Conversion (%) =

$$\frac{\text{Moles of isobutylene or tertiary butanol reacted}}{\text{Moles of isobutylene or tertiary butanol fed}} \times 100$$

Selectivity (%) =

$$\frac{\text{Moles of the methacrolein formed}}{\text{Moles of isobutylene or tertiary butanol reacted}} \times 100$$

One-pass yield (%) =

$$\frac{\text{Moles of the methacrolein formed}}{\text{Moles of isobutylene or tertiary butanol fed}} \times 100$$

EXAMPLE 1

1456 g of cobalt nitrate and 202 g of ferric nitrate were dissolved in 1000 ml of distilled water, and 243 g of bismuth nitrate was added to 120 ml of distilled water acidified with 30 ml of concentrated nitric acid.

Separately, 1059 g of ammonium paramolybdate and 265 g of ammonium paratungstate were dissolved in 3,000 ml of distilled water heated with stirring. The resulting solution is designated as solution A.

A mixture of the two solutions aforementioned was added dropwise to the solution A, and subsequently, a solution of 39.0 g of cesium nitrate in 100 ml of distilled water and a solution of 203 g of silica sol containing 20% by weight of silica were added.

The resulting suspension was heated with stirring and evaporated to dryness, pulverized, and then molded into a hollow cylindrical shape having an outside diameter (D) of 6.0 mm, an inside diameter (d) of 1.0 mm, and a length (L) of 6.6 mm. The molded product was calcined in the air at 500° C. for 6 hours.

The resulting catalyst had the following elemental composition excepting oxygen (atomic ratio).

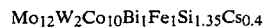

$Mo_{12}W_2Co_{10}Bi_1Fe_1Si_{1.35}Cs_{0.4}$ 1500 ml of the resulting catalyst was filled in a steel reaction tube having a diameter of 25.4 mm. At a reaction temperature of 340° C., a gaseous mixture composed of 6% by volume of isobutylene, 13.2% by volume of oxygen, 15% by volume of steam and 65.8% by volume of nitrogen was introduced into the reaction tube and reacted at a space velocity of 1600 $hr^{-1}$. After 100 hours of reaction time elapsed, the pressure drop and $\Delta T$ (the difference between the reaction temperature and the temperature of the hot spot), and the yields of the products are shown in Table 1.

EXAMPLE 2

The procedure of Example 1 was repeated except that the inside diameter of the catalyst was changed to 2.0 mm. After 100 hours of reaction time elapsed, the pressure drop and $\Delta T$, and the yields of the products are shown in Table 1.

EXAMPLE 3

The procedure of Example 1 was repeated except that the inside diameter of the catalyst was changed to 3.0 mm. After 100 hours of reaction time elapsed, the pressure drop and $\Delta T$, and the yields of the products are shown in Table 1.

COMPARATIVE EXAMPLE 1

The catalyst composition prepared in Example 1 was molded into a solid cylindrical shape having diameter of 6.0 mm and a length of 6.6 mm, and calcined in the same way as in Example 1. By using the resulting catalyst, the same reaction as in Example 1 was carried out. After 100 hours of reaction time elapsed, the pressure drop and $\Delta T$, and the yields of the products are shown in Table 1.

COMPARATIVE EXAMPLE 2

The procedure of Example 1 was repeated except that the inside diameter of the catalyst was changed to 0.5 mm. After 100 hours of reaction time elapsed, the pressure drop and $\Delta T$, and the yields of the products are shown in Table 1.

EXAMPLE 4

A catalyst molded in the shape of a hollow cylinder having an outside diameter (D) of 4.0 mm, an inside diameter (d) of 1.0 mm and a length (L) of 4.4 mm was prepared in the same way as in Example 1 except that rubidium nitrate and potassium nitrate were used instead of cesium nitrate. The resulting catalyst had the following elemental composition (atomic ratio) excepting oxygen.

$Mo_{12}W_2Bi_3Fe_1Co_7Si_{1.35}Rb_{0.4}K_{0.1}$

By using this catalyst, the same reaction as in Example 1 was carried out.

After 100 hours of reaction time elapsed, the pressure drop and $\Delta T$, and the yields of the products are shown in Table 1.

COMPARATIVE EXAMPLE 3

The catalyst composition prepared in Example 4 was molded into the shape of a solid cylinder having a diameter of 4.0 mm and a length of 4.4 mm, and calcined in the same way as in Example 1. By using the resulting catalyst, the same reaction as in Example 1 was carried out.

After 100 hours of reaction time elapsed, the pressure drop and $\Delta T$, and the yields of the products are shown in Table 1.

EXAMPLE 5

A catalyst molded in the shape of a hollow cylinder having an outside diameter (D) of 8.0 mm, an inside diameter (d) of 3.0 mm and a length (L) of 8.8 mm was prepared in the same way as in Example 1 except that thallium nitrate was used instead of cesium nitrate, and phosphoric acid was added after ammonium paratungstate added. The resulting catalyst had the following elemental composition (atomic ratio) excepting oxygen.

$Mo_{12}W_2Co_{10}Bi_1Fe_1Si_{1.35}Tl_{0.4}P_{0.2}$

By using this catalyst, the same reaction as in Example 1 was carried out.

After 100 hours of reaction time elapsed, the pressure drop and $\Delta T$, and the yields of the products are shown in Table 1.

COMPARATIVE EXAMPLE 4

The catalyst composition prepared in Example 5 was molded into the shape of a solid cylinder having a diameter of 8.0 mm and a length of 8.8 mm, and calcined in the same way as in Example 5. By using the resulting catalyst, the same reaction as in Example 1 was carried out.

After 100 hours of reaction time elapsed, the pressure drop and $\Delta T$, and the yields of the products are shown in Table 1.

EXAMPLE 6

A catalyst molded in the shape of a hollow cylinder having an outside diameter (D) of 6.0 mm, an inside diameter of 2.0 mm and a length (L) of 6.6 mm was prepared in the same way as in Example 1 except that nickel nitrate was used instead of cobalt nitrate and magnesium nitrate and calcium nitrate were used together with cerium nitrate. This catalyst had the following elemental composition (atomic ratio) excepting oxygen.

$Mo_{12}W_2Ni_8Bi_1Fe_1Si_{1.35}Cs_{0.2}Mg_1Ca_1$

By using the resulting catalyst, the same reaction as in Example 1 was carried out.

After 100 hours of reaction time elapsed, the pressure drop and $\Delta T$, and the yields of the products are shown in Table 2.

EXAMPLE 7

The reaction procedure of Example 6 was continued for 2000 hours. The results are shown in Table 2.

COMPARATIVE EXAMPLES 5 AND 6

The catalyst composition prepared in Example 6 was molded into the shape of a solid cylinder having a diameter of 6.0 mm and a length of 6.6 mm. By using the resulting catalyst, the same reaction as in Example 1 was carried out.

After the reaction times of 100 hours and 2000 hours elapsed, the pressure drops and $\Delta T$, and the yields of the products are shown in Table 2, respectively.

EXAMPLE 8

A catalyst molded into the shape of a hollow cylinder having an outside diameter (D) of 6.0 mm, an inside diameter (d) of 2.0 mm, and a length (L) of 6.6 mm was prepared in the same way as in Example 1 except that ammonium paratungstate was not used, lead nitrate was added before the addition of silica sol and the calcination temperature and time were 650° C. and 4 hours. The resulting catalyst had the following elemental composition (atomic ratio) excepting oxygen.

$Mo_{12}Co_7Bi_1Fe_3Si_{11}Cs_{0.1}Pb_1$

By using this catalyst, the same reaction as in Example 1 was carried out.

The pressure drop and $\Delta T$ during the reaction, and the yields of the products are shown in Table 2.

TABLE 1

| Example (Ex.) or Comparative Example (CEx.) | Shape of the catalyst | | | Conversion of iso-butylene (mole %) | Selectivity (mole %) | | One-pass yield (mole %) | | $\Delta T$ (°C.) | Pressure drop (mm Hg) |
|---|---|---|---|---|---|---|---|---|---|---|
| | D (mm) | d (mm) | L (mm) | | methacrolein | methacrylic acid | methacrolein | methacrylic acid | | |
| Ex. 1 | 6.0 | 1.0 | 6.6 | 99.0 | 85.8 | 3.3 | 84.9 | 3.3 | 76 | 135 |
| Ex. 2 | 6.0 | 2.0 | 6.6 | 98.7 | 86.4 | 3.2 | 85.3 | 3.2 | 71 | 115 |
| Ex. 3 | 6.0 | 3.0 | 6.6 | 98.3 | 86.9 | 2.8 | 85.4 | 2.8 | 64 | 95 |
| CEx. 1 | 6.0 | — | 6.6 | 98.3 | 84.3 | 3.6 | 82.9 | 3.5 | 85 | 145 |
| CEx. 2 | 6.0 | 0.5 | 6.6 | 98.5 | 84.3 | 3.5 | 83.0 | 3.4 | 84 | 143 |
| Ex. 4 | 4.0 | 1.0 | 4.4 | 99.2 | 86.0 | 3.6 | 85.3 | 3.6 | 83 | 175 |
| CEx. 3 | 4.0 | — | 4.4 | 98.5 | 84.4 | 3.8 | 83.1 | 3.8 | 91 | 215 |
| Ex. 5 | 8.0 | 3.0 | 8.8 | 95.1 | 86.4 | 2.6 | 82.2 | 2.5 | 59 | 70 |
| CEx. 4 | 8.0 | — | 8.8 | 94.3 | 85.1 | 2.9 | 80.2 | 2.7 | 68 | 85 |

COMPARATIVE EXAMPLE 7

The catalyst composition prepared in Example 8 was molded into the shape of a solid cylinder having a diameter of 6.0 mm and a length of 6.6 mm, and calcined in the same way as in Example 8. By using the resulting catalyst, the same reaction as in Example 1 was carried out.

The pressure drop and ΔT during the reaction, and the yields of the products are shown in Table 2.

in the same way as in Example 10. By using the resulting catalyst, the same reaction as in Example 1 was carried out.

The pressure drop and ΔT during the reaction, and the yields of the products are shown in Table 4.

EXAMPLE 11

A catalyst molded in the shape of a hollow cylinder having an outside diameter (D) of 6.0 mm, an inside diameter (d) of 2.0 mm and a length (L) of 6.6 mm was

TABLE 2

| Example (Ex.) or Comparative Example (CEx.) | Shape of the catalyst | | | Reaction time (hrs) | Conversion of iso-butylene (mole %) | Selectivity (mole %) | | One-pass yield (mole %) | | ΔT (°C.) | Pressure drop (mmHg) |
|---|---|---|---|---|---|---|---|---|---|---|---|
| | D (mm) | d (mm) | L (mm) | | | Meth-acrolein | Meth-acrylic acid | Meth-acrodein | Meth-acrylic acid | | |
| Ex. 6 | 6.0 | 2.0 | 6.6 | 100 | 98.5 | 80.9 | 3.8 | 79.7 | 3.7 | 76 | 115 |
| Ex. 7 | 6.0 | 2.0 | 6.6 | 2000 | 98.3 | 81.2 | 3.6 | 79.8 | 3.5 | 71 | 117 |
| CEx. 5 | 6.0 | — | 6.6 | 100 | 98.0 | 77.5 | 4.3 | 76.0 | 4.2 | 92 | 145 |
| CEx. 6 | 6.0 | — | 6.6 | 2000 | 95.9 | 77.6 | 4.0 | 74.4 | 3.8 | 85 | 156 |
| Ex. 8 | 6.0 | 2.0 | 6.6 | 100 | 93.2 | 79.3 | 3.5 | 73.9 | 3.3 | 76 | 115 |
| CEx. 7 | 6.0 | — | 6.6 | 100 | 92.5 | 76.1 | 4.1 | 70.4 | 3.8 | 93 | 145 |

EXAMPLE 9

The same catalyst composition as in Example 1 was molded into the shape of a hollow cylinder having an outside diameter (D) of 5.0 mm, an inside diameter (d) of 2.0 mm and a length (L) of 5.5 mm. By using this catalyst, the same reaction as in Example 1 was carried out. The pressure drop during the reaction was the same as in Comparative Example 1. The ΔT and the yields of the products are shown in Table 3.

prepared in the same way as in Example 1 except that ammonium paratungstate was not used, potassium nitrate was used instead of cesium nitrate, aluminium nitrate was used instead of silica sol and the calcination was carried out at 600° C. for 6 hours in the air. The resulting catalyst had the following elemental composition (atomic ratio) excepting oxygen.

$$Mo_{12}Co_5Bi_1Fe_{12}Al_1K_{0.5}$$

TABLE 3

| Example (Ex.) or Comparative Example (CEx.) | Shape of the catalyst | | | Conversion of isobutylene (mole %) | Selectivity (mole %) | | One-pass yield (%) | | ΔT (°C.) |
|---|---|---|---|---|---|---|---|---|---|
| | D (mm) | d (mm) | L (mm) | | Meth-acrolein | Meth-acrylic acid | Meth-acrolein | Meth-acrylic acid | |
| Ex. 9 | 5.0 | 2.0 | 5.5 | 99.1 | 86.5 | 3.3 | 85.7 | 3.3 | 77 |
| CEx. 1 | 6.0 | — | 6.6 | 98.3 | 84.3 | 3.6 | 82.9 | 3.5 | 85 |

EXAMPLE 10

A catalyst molded into the shape of a hollow cylinder having an outside diameter (D) of 6.0 mm, an inside diameter (d) of 2.0 mm and a length (L) of 6.6 mm was prepared in the same way as in Example 1 except that ammonium paratungstate and cesium nitrate were not used and nickel nitrate and titanium dioxide were used instead of cobalt nitrate and silica sol, and that antimony trioxide was added together with ammonium paramolybdate and stannic oxide and tellurium dioxide were added before the additon of titanium dioxide. The resulting catalyst had the following elemental composition (atomic ratio) excepting oxygen.

$$Mo_{12}Ni_6Bi_1Fe_3Ti_1Sb_{2.0}Sn_1Te_{0.5}$$

By using the resulting catalyst, the same reaction as in Example 1 was carried out.

The pressure drop and ΔT during the reaction, and the yields of the products are shown in Table 4.

COMPARATIVE EXAMPLE 8

The catalyst composition prepared in Example 10 was molded into the shape of a solid cylinder having a diameter of 6.0 mm and a length of 6.6 mm, and calcined By using the resulting catalyst, the same reaction as in Example 1 except that the steam concentration was zero and the nitrogen concentration was 80.8% in the starting gas composition was carried out.

The pressure drop and ΔT during the reaction, and the yields of the products are shown in Table 4.

COMPARATIVE EXAMPLE 9

The catalyst composition prepared in Example 11 was molded into the shape of a solid cylinder having a diameter of 6.0 mm and a length of 6.6 mm, and calcined in the same way as in Example 11. By using the resulting catalyst, the same reaction as in Example 11 was carried out.

The pressure drop and ΔT during the reaction, and the yields of the products are shown in Table 4.

EXAMPLE 12

A catalyst molded in the shape of a hollow cylinder having an outside diameter (D) of 6.0 mm, an inside diameter (d) of 2.0 mm and a length (L) of 6.6 mm was prepared in the same way as in Example 1 except that ammonium paratungstate was not used, zirconium nitrate was used instead of silica sol and in the final stage cerium nitrate, manganese nitrate, zinc nitrate and niobium pentaoxide were added. The resulting catalyst had the following elemental composition (atomic ratio) excepting oxygen.

$$Mo_{12}Co_6Bi_1Fe_1Zr_1Cs_{0.4}Ce_1Mn_1Zn_1Nb_{0.5}$$

By using the resulting catalyst, the same reaction as in Example 1 was carried out.

The pressure drop and ΔT during the reaction, and the yields of the products are shown in Table 4.

COMPARATIVE EXAMPLE 10

The catalyst composition prepared in Example 12 was molded into the shape of a solid cylinder having a diameter of 6.0 mm and a length of 6.6 mm. By using the resulting catalyst, the same reaction as in Example 1 was carried out.

The pressure drop and ΔT during the reaction, and the yields of the products are shown in Table 4.

TABLE 4

| Example (Ex.) or Comparative Example (CEx.) | Shape of the catalyst | | | Conversion of iso-butylene (mole %) | Selectivity (mole %) | | One-pass yield (mole %) | | ΔT (°C.) | Pressure drop (mmHg) |
|---|---|---|---|---|---|---|---|---|---|---|
| | D (mm) | d (mm) | L (mm) | | meth-acrolein | meth-acrylic acid | meth-acrolein | meth-acrylic acid | | |
| Ex. 10 | 6.0 | 2.0 | 6.6 | 90.3 | 78.4 | 3.2 | 70.8 | 2.9 | 83 | 115 |
| CEx. 8 | 6.0 | — | 6.6 | 89.5 | 75.5 | 3.5 | 67.6 | 3.1 | 93 | 145 |
| Ex. 11 | 6.0 | 2.0 | 6.6 | 95.1 | 76.4 | 4.1 | 72.7 | 3.9 | 91 | 115 |
| CEx. 9 | 6.0 | — | 6.6 | 94.5 | 72.7 | 5.0 | 68.7 | 4.7 | 101 | 145 |
| Ex. 12 | 6.0 | 2.0 | 6.6 | 92.7 | 74.3 | 5.7 | 68.9 | 5.3 | 92 | 115 |
| CEx. 10 | 6.0 | — | 6.6 | 92.1 | 71.0 | 6.5 | 65.4 | 6.0 | 100 | 145 |

EXAMPLE 13

Tertiary butanol was oxidized instead of isobutylene using the catalyst obtained in Example 2. Reaction condition was the same as in Example 1 except that tertiary butanol concentration was 6% by volume in the starting gas composition.

The pressure drop and ΔT during the reaction, and the yields of the products are shown in Table 5.

COMPARATIVE EXAMPLE 11

By using the catalyst prepared in Comparative Example 1, the same reaction as in Example 13 was carried out.

The pressure drop and ΔT during the reaction, and the yield of the products are shown in Table 5.

TABLE 5

| Example (Ex.) or Comparative Example (CEx.) | Shape of the catalyst | | | Conversion of tert.butanol (mole %) | One-pass yield (mole %) | | | ΔT (°C.) | Pressure drop (mmHg) |
|---|---|---|---|---|---|---|---|---|---|
| | D (mm) | d (mm) | L (mm) | | Meth-acrolein | Meth-acrylic acid | Isobutylene | | |
| Ex. 13 | 6.0 | 2.0 | 6.6 | 100 | 85.8 | 2.9 | 1.5 | 67 | 115 |
| CEx. 11 | 6.0 | — | 6.6 | 100 | 83.2 | 3.4 | 1.9 | 79 | 145 |

What is claimed is:

1. A catalyst for manufacturing methacrolein by the vapor phase oxidation of isobutylene or tertiary butanol, said catalyst having the composition represented by the following formula $$Mo_aW_bBi_cFe_dA_eB_fC_gD_hO_x$$

wherein
A represents at least one element selected from the group consisting of nickel and cobalt,
B represents at least one element selected from the group consisting of alkali metals, alkaline earth metals and thallium,
C represents at least one element selected from the group consisting of tellurium, antimony, tin, cerium, lead, manganese and zinc,
D represents at least one element selected from the group consisting of silicon, aluminum, zirconium and titanium,
a, b, c, d, e, f, g, h, and x respectively represent the atomic ratios of Mo, W, Bi, Fe, A, B, C, D, and O, and when
a is fixed at 12,
b is from 0 to 10,
c is from 0.1 to 10,
d is from 0.1 to 20,
e is from 2 to 20,
f is from 0 to 10,
g is greater than 0 to 4,
h is from 0 to 30 and
x is a number determined by the atomic valences of the individual elements,
and being molded in the shape of a hollow cylinder having an outside diameter of 3.0 to 10.0 mm, an inside diameter 0.1 to 0.7 times the outside diameter and a length 0.5 to 2.0 times the outside diameter.

2. The catalyst of claim 1 wherein $$\frac{D - d}{2}$$

is from 1.0 to 4.0 mm where D is the outside diameter of the hollow cylinder and d is the inside diameter of the hollow cylinder.

3. The catalyst of claim 1 wherein each of f and h are greater than 0.

4. The catalyst composition of claim 3 wherein A represents Co, B represents Cs, C represents Pb and D represents Si.

5. The catalyst according to claim 1 wherein f is 0, h is greater than 0, A represents Ni, C represents Sb, Sn and Te, and D represents Ti.

6. The catalyst according to claim 3 wherein A represents Co, B represents Cs, C represents Ce, Mn, and Zn, and D represents Zr, said catalyst further including Nb.

* * * * *